(12) United States Patent
Jayaraman et al.

(10) Patent No.: US 11,219,378 B2
(45) Date of Patent: Jan. 11, 2022

(54) METHOD AND DEVICE FOR CONTINUOUS BLOOD PRESSURE MONITORING AND ESTIMATION

(71) Applicant: Tata Consultancy Services Limited, Mumbai (IN)

(72) Inventors: Srinivasan Jayaraman, Bangalore (IN); Balamuralidhar Purushothaman, Bangalore (IN); Midhun P Unni, Bangalore (IN); Aniruddha Sinha, Kolkata (IN); Arpan Pal, Kolkata (IN); Ramesh Kumar Ramakrishnan, Bangalore (IN)

(73) Assignee: Tata Consultancy Services Limited, Mumbai (IN)

( * ) Notice: Subject to any disclaimer, the term of this patent is extended or adjusted under 35 U.S.C. 154(b) by 772 days.

(21) Appl. No.: 15/255,643

(22) Filed: Sep. 2, 2016

(65) Prior Publication Data

US 2017/0065191 A1 Mar. 9, 2017

(30) Foreign Application Priority Data

Sep. 4, 2015 (IN) .......................... 3417/MUM/2015

(51) Int. Cl.
*A61B 5/021* (2006.01)
*A61B 5/00* (2006.01)
(Continued)

(52) U.S. Cl.
CPC ........ *A61B 5/02133* (2013.01); *A61B 5/0022* (2013.01); *A61B 5/021* (2013.01);
(Continued)

(58) Field of Classification Search
CPC ............ A61B 5/02007; A61B 5/02108; A61B 5/02028
See application file for complete search history.

(56) References Cited

U.S. PATENT DOCUMENTS 8,808,186 B2 8/2014 Banet et al.
2003/0135124 A1* 7/2003 Russell .............. A61B 5/02007
600/500

(Continued)

OTHER PUBLICATIONS

Atlas. G. et al. (Dec. 2014), "Pulsatile Aortic Pressure-Flow Analysis using Fractional Calculus for Minimaliy-invasive Applications," *Journal of Biomedical Engineering and Biosciences*, vol. 1; pp. 1-7.

*Primary Examiner* — Tse W Chen
*Assistant Examiner* — Michael A Catina
(74) *Attorney, Agent, or Firm* — Finnegan, Henderson, Farabow, Garrett & Dunner, LLP

(57) ABSTRACT

A method and device is provided for the continuous estimation of the blood pressure using a noninvasive technique. The method involves sensing of the displacement signal generated by the palpation of the radial artery. The radial artery is modelled as a cylindrical voight type viscoelastic tissue for the estimation of the personalized blood pressure. The model includes the displacement signal and a set of parameters as an input. The set of parameters include a mean radius of the artery, a radius at zero mmHg, a viscoelastic damping parameter, an elasticity of the artery and a thickness of wall of artery. The method involves the optimization of the set of parameters using heuristic optimization techniques, which helps in the estimation of the systolic and diastolic blood pressure. The method and device can also be personalized for individualized monitoring and estimation of the blood pressure of the person.

7 Claims, 4 Drawing Sheets

(51) Int. Cl.
*A61B 5/02* (2006.01)
*G01L 9/00* (2006.01)

(52) U.S. Cl.
CPC ...... *A61B 5/02007* (2013.01); *A61B 5/02108* (2013.01); *A61B 5/6824* (2013.01); *A61B 5/6828* (2013.01); *A61B 5/6831* (2013.01); *A61B 5/7225* (2013.01); *A61B 5/7271* (2013.01); *A61B 5/7278* (2013.01); *A61B 5/743* (2013.01); *G01L 9/008* (2013.01)

(56) References Cited

U.S. PATENT DOCUMENTS

2013/0035600 A1 2/2013 Wei
2014/0358015 A1 12/2014 Cohen et al.

\* cited by examiner

METHOD AND DEVICE FOR CONTINUOUS BLOOD PRESSURE MONITORING AND ESTIMATION

CROSS-REFERENCE TO RELATED APPLICATIONS AND PRIORITY

The present application claims priority from Indian non-provisional specification no. 3417/MUM/2015 filed on 4 Sep. 2015, the complete disclosure of which, in its entirety is herein incorporated by references.

TECHNICAL FIELD

The present application generally relates to blood pressure measurement. More particularly, but not specifically, the invention provides a method and device for continuously monitoring and estimating blood pressure of a person using displacement signal generated by palpation of arteries.

BACKGROUND

The blood pressure measurement is one of the techniques to monitor the health of an individual. Typically, blood pressure is characterized by two readings, the systolic and diastolic blood pressures. The systolic blood pressure is the pressure as the heart contracts and is the higher of the two pressures. The diastolic blood pressure is the pressure when the heart relaxes and fills with blood in preparation for another contraction. The high blood pressure can result in headache, vision problem, nose bleeding etc. The high blood pressure may indicate few problems such as type II diabetes kidney disease or toxemia. The low blood pressure which results in dizziness, blurred vision, fainting, which may be an indicator to certain diseases like allergic reaction, heart problems, shock, etc. Thus it is necessary to continuously monitor and measure the blood pressure of a patient or a person.

The conventional non-invasive blood pressure measurement methods require a cuff to be fastened on a particular part of a body, and each group of measurement data is obtained after going through periods of inflation and deflation of the cuff. Therefore, it is impossible to continuously monitor a patient's blood pressure without interruption. In addition to that these methods are susceptible to noise.

Another approach for measuring blood pressure uses a sphygmomanometer. This is one of the auscultatory methods to measure the blood pressure. A typical sphygmomanometer has an occluding cuff capable of being wrapped around a patient's arm; a pump for inflating the cuff; either an aneroid or mercury gravity sphygmomanometer to measure pressure in the cuff; and a stethoscope or other system for detecting Korotkoff sounds. Such devices are widely used in hospitals and doctors' offices for making routine blood pressure measurements but are not well adapted to providing continuous blood pressure monitoring.

Another method for measuring blood pressure is the oscillometric method. Oscillometric blood pressure measurements are made by using a transducer to detect and measure pressure waves in a pressure cuff as blood surges through an artery constricted by the pressure cuff. Many currently available digital blood pressure monitors use the oscillometric method for determining blood pressure. The oscillometric method is not ideal for continuous blood pressure monitoring because it typically cannot produce an updated blood pressure reading more frequently than about once every 30 seconds. Further, the cuff compresses underlying tissues. Over an extended period of time this can cause tissue damage.

Continuous measurement of blood pressure by means of optically based pressure transducer tips, inserted into the blood stream using a catheter, have also been proposed. Several other methods exist for the determination of continuous non-invasive blood pressure monitoring. However, none of these has been widely accepted. Problems include susceptibility to motion, questionable accuracy, and poor sensor locations.

Another non-invasive method of estimating the BP from the physiological signal is using multimode approach. For example, acquire more than one signal like ECG and PPG or ECG and PCG or PCG and PPG. Here we have to use multiple sensor, which is an cumbersome method and less accuracy In addition to those, cuff-based methods may not yield representative blood pressure during sleep as repeated inflations induce arousal reactions, leading to non-representative overestimated BP values. Therefore, the development of novel technologies that reduce the recurrent use of pneumatic cuffs is clearly justified.

The above-mentioned prior art lacks the advantages of a continuous blood pressure monitoring system that is capable of being worn for continual periods, whilst offering the patient complete mobility.

SUMMARY

Embodiments of the present disclosure present technological improvements as solutions to one or more of the above-mentioned technical problems recognized by the inventors in conventional systems.

The present application provides a processor implemented method for continuously monitoring and estimating blood pressure of a person. A displacement generated by the palpation of an artery of the person is sensed using a piezoelectric sensor. The displacement signal is then amplified, filtered to generate a processed displacement signal. The processed displacement signal is then sent as a first input to a processor. A set of parameters are provided as a second input to the processor. The set of parameters include at least one of a mean radius of the artery, a radius at zero mmHg, a viscoelastic damping parameter, an elasticity of the artery and a thickness of wall of the artery. A blood pressure waveform is then generated by the processor as an output using the set of parameters and the processed displacement signal. Finally, the processor estimates a systolic blood pressure and a diastolic blood pressure using a maximum and minimum values of the blood pressure waveform.

According to another embodiment, the invention also provides a processor implemented method where the continuous monitoring and estimation of the blood pressure is personalized specific to the person. In this method, the set of parameters are estimated using a medical history related to systolic and diastolic blood pressure of the person and the processed displacement signal. The viscoelastic damping parameter, the mean radius of the artery and the radius at zero mmHg are then optimized by the processor using a heuristic optimization technique. A blood pressure waveform is then generated by the processor as an output using the optimized viscoelastic damping parameter, the optimized mean radius of the artery and the optimized radius at zero mmHg, the elasticity of the artery, the thickness of the wall of the arteries, and the processed displacement signal. Finally, the processor estimates a systolic blood pressure and a diastolic blood pressure using a maximum and minimum values of the blood pressure waveform.

According to an embodiment, the invention also provides a device for continuous monitoring and estimation of the blood pressure of the person. The device includes a strap worn by the person, a piezoelectric sensor, a user interface and a processor. The piezoelectric sensor is present on the strap. The piezoelectric sensor senses a displacement signal generated by the palpation of an artery of the person. The user interface provides a set of parameters. The set of parameters include at least one of a mean radius of the artery, a radius at zero mmHg, a viscoelastic damping parameter, an elasticity of the artery and a thickness of wall of the artery. The processor performs the step as mentioned in the above paragraph to estimate the systolic and the diastolic blood pressure of the person for both the generalized and personalized case.

In another embodiment, a non-transitory computer-readable medium having embodied thereon a computer program for continuously monitoring and estimating blood pressure of a person has also been provided. A displacement generated by the palpation of an artery of the person is sensed using a piezoelectric sensor. The displacement signal is then amplified, filtered to generate a processed displacement signal. The processed displacement signal is then sent as a first input to a processor. A set of parameters are provided as a second input to the processor. The set of parameters include at least one of a mean radius of the artery, a radius at zero mmHg, a viscoelastic damping parameter, an elasticity of the artery and a thickness of wall of the artery. A blood pressure waveform is then generated by the processor as an output using the set of parameters and the processed displacement signal. Finally, the processor estimates a systolic blood pressure and a diastolic blood pressure using a maximum and minimum values of the blood pressure waveform.

BRIEF DESCRIPTION OF THE DRAWINGS

The foregoing summary, as well as the following detailed description of preferred embodiments, are better understood when read in conjunction with the appended drawings. For the purpose of illustrating the invention, there is shown in the drawings exemplary constructions of the invention; however, the invention is not limited to the specific methods and devices disclosed. In the drawings.

Figure 1:
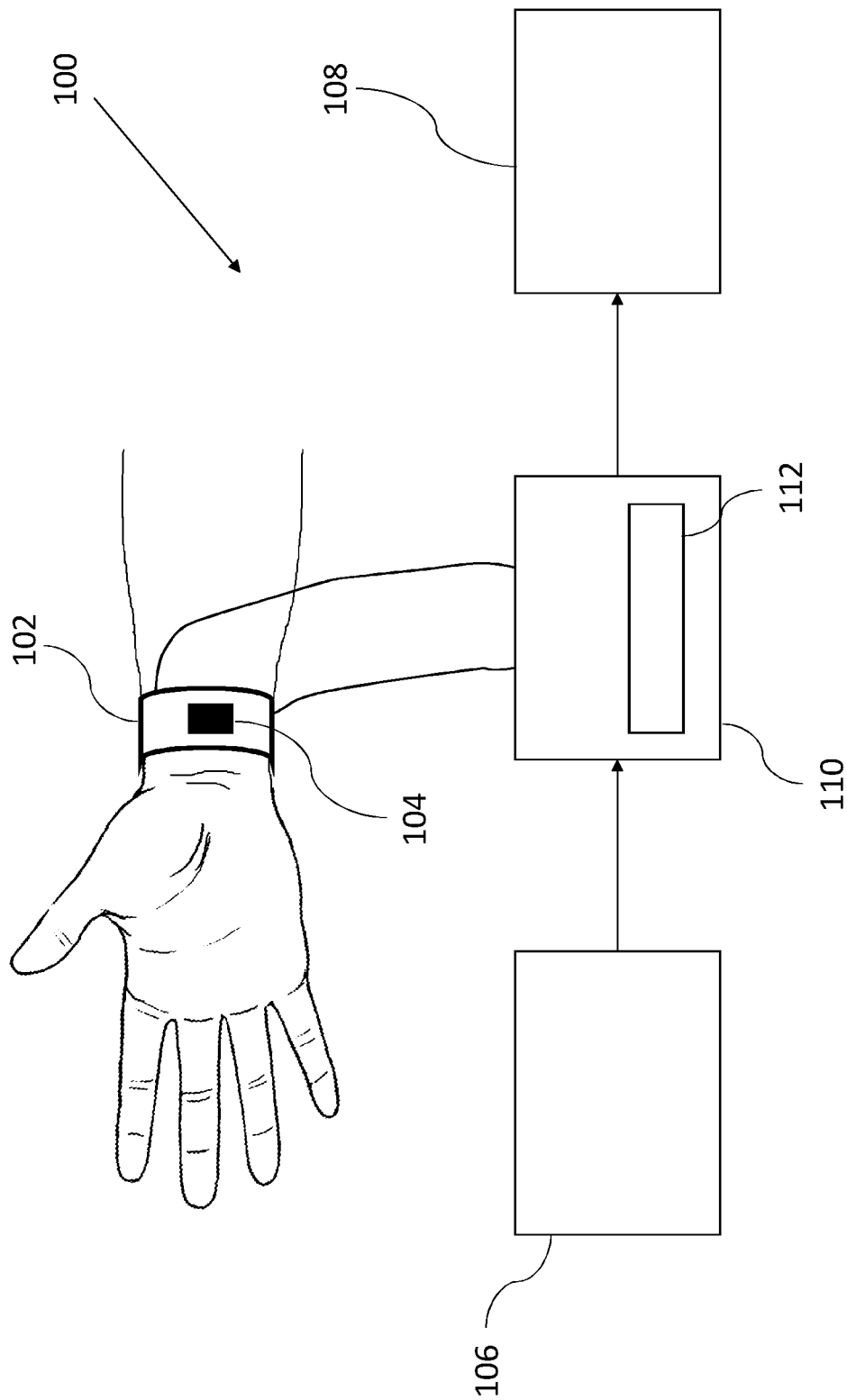
FIG. 1 shows a block diagram illustrating a blood pressure monitoring and estimating device attached to the wrist of a person in accordance with an embodiment of the invention.

The Figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE INVENTION

Some embodiments of this invention, illustrating all its features, will now be discussed in detail.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present invention, the preferred, systems and methods are now described. In the following description for the purpose of explanation and understanding reference has been made to numerous embodiments for which the intent is not to limit the scope of the invention.

One or more components of the invention are described as module for the understanding of the specification. For example, a module may include self-contained component in a hardware circuit comprising of logical gate, semiconductor device, integrated circuits or any other discrete component. The module may also be a part of any software programme executed by any hardware entity for example processor. The implementation of module as a software programme may include a set of logical instructions to be executed by a processor or any other hardware entity.

The disclosed embodiments are merely exemplary of the invention, which may be embodied in various forms.

Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk.

The present application provides a method for continuously monitoring and estimating blood pressure of a person. A displacement generated by the palpation of an artery of the person is sensed using a piezoelectric sensor. The displacement signal is then amplified, filtered to generate a processed displacement signal. The processed displacement signal is then sent as a first input to a processor. A set of parameters are provided as a second input to the processor. The set of parameters include at least one of a mean radius of the artery, a radius at zero mmHg, a viscoelastic damping parameter, an elasticity of the artery and a thickness of wall of the artery. A blood pressure waveform is then generated by the processor as an output using the set of parameters and the processed displacement signal. Finally, the processor estimates a systolic blood pressure and a diastolic blood pressure using a maximum and minimum values of the blood pressure waveform.

According to another embodiment, the invention also provides a method where the continuous monitoring and estimation of the blood pressure is personalized specific to the person. In this method, the set of parameters are estimated using a medical history related to systolic and diastolic blood pressure of the person and the processed displacement signal. The viscoelastic damping parameter, the mean radius of the artery and the radius at zero mmHg are then optimized by the processor using a heuristic optimization technique. A blood pressure waveform is then generated by the processor as an output using the optimized viscoelastic damping parameter, the optimized mean radius of the artery and the optimized radius at zero mmHg, the elasticity of the artery, the thickness of the wall of the arteries, and the processed displacement signal. Finally, the processor estimates a systolic blood pressure and a diastolic blood pressure using a maximum and minimum values of the blood pressure waveform.

According to an embodiment of the present invention, a device 100 for monitoring and estimating blood pressure of a person is shown in FIG. 1. The device 100 is configured to continuously monitor the blood pressure of the person using a non-invasive technique. The device senses and analyzes pressure transmission properties from the radial artery of the person, thereby estimating other characteristics, such as a diastolic pressure, a systolic pressure, a mean blood pressure of the person. The device 100 is continuously monitoring the arterial pulse palpation in a non-invasive manner to estimate the blood pressure of the person.

According to an embodiment of the present invention, the device 100 includes a strap 102, a piezoelectric sensor 104 present on the strap 102, a user interface 106, a display screen 108, a processor 110 and a signal processing module 112 as shown in FIG. 1. The processor 110 is electronically coupled with the user interface 106 and the display screen 108 through a wired or a wireless medium. The signal processing module 112 is configured to take input from the piezoelectric sensor 104 to generate a processed displacement signal. The processor 110 is configured to receive the processed displacement and the set of parameters from the user interface 106 to estimate the blood pressure and display it on the display screen 108. It should be appreciated that in another embodiment, the display screen 108 and the user interface 106 are the same. i.e., the display screen 108 can be converted in to the user interface 106 and used to provide the input. The display screen 108 can be a touch screen or any other type of display screen available in the market.

Normally, the strap 102 is worn by the person on the wrist as shown in FIG. 1. The piezoelectric sensor 104 is attached to the strap 102 in such a way that the piezoelectric sensor 104 can easily sense the pulse palpation signal from the person's body. In a person, the palpation signal are generated at an average of 72 palpations per minute. Thus the measurement of arterial palpation and blood pressure estimation corresponding to the palpation results in continuous monitoring and estimation of the blood pressure of the person. Arterial pulse palpation signal can be accurate at various places in the human body, however for continuous monitoring of the pulse and the blood pressure an adequate position has to be adapted. In an embodiment of the invention, the strap 102 is present on the wrist of the person. To be more precise, the region of interest includes 1-5 cm below the dorsal side of the styloid process landmark on the surface of the wrist. Though it should be appreciated a person having original skill in the art can easily design the device 100 in such a way that the strap 102 can also be worn by the person at any other part of the body such as leg, arms etc. It should also be appreciated the device 100 can also be implement in any other form other than the strap arrangement.

Figure 2:
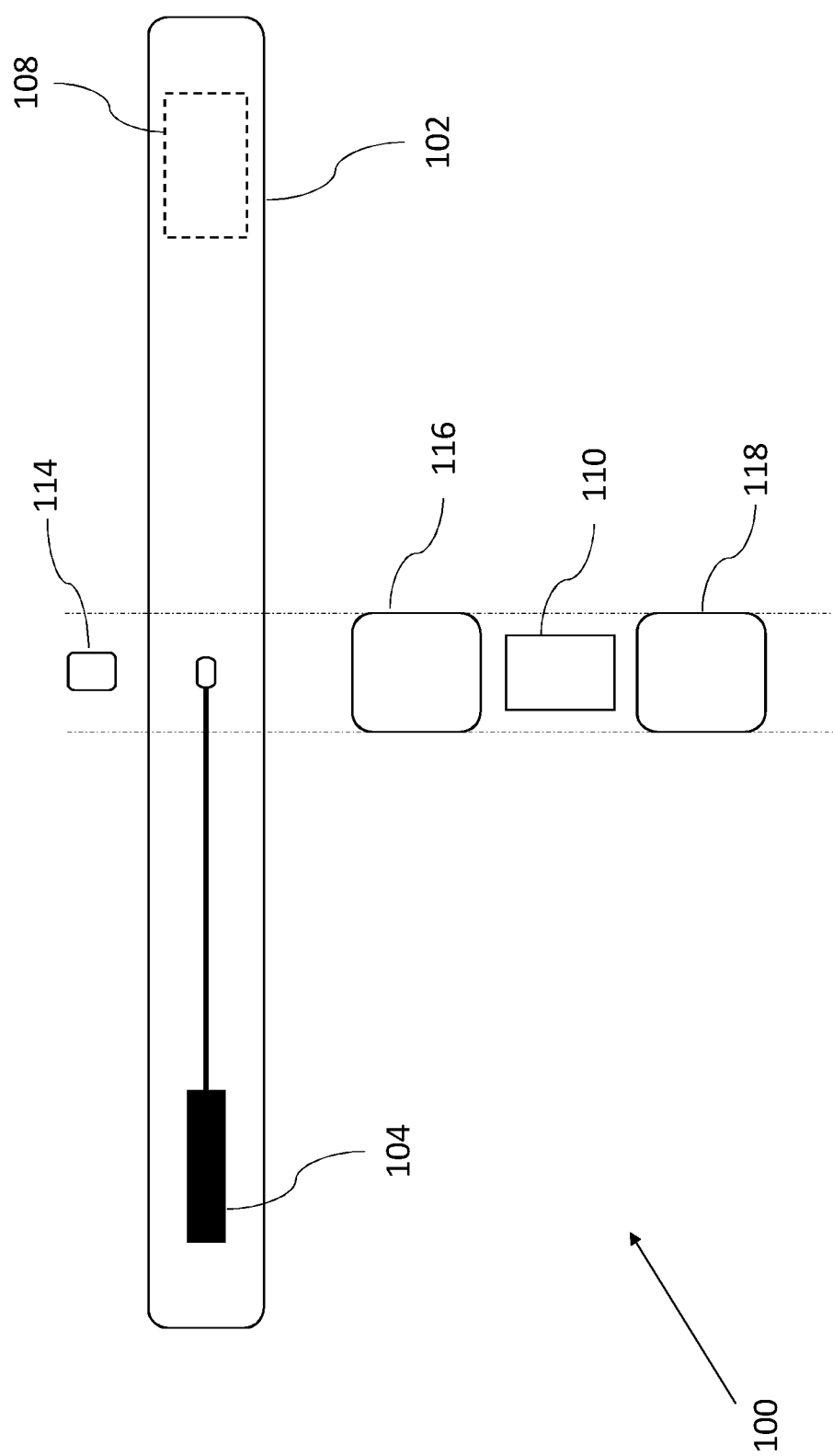
FIG. 2 shows a schematic diagram illustrating various parts of the blood pressure monitoring and estimating device in accordance with an embodiment of the invention.

According to an embodiment of the invention, an exploded view of the device 100 for monitoring and estimating the blood pressure shown in FIG. 2. The figures shows the device 100 including a screw 114, an upper cover 116, a lower cover 118 and the processor 110 which can be fitted between the upper cover 116 and the lower cover 118. The strap 102 also include the piezoelectric sensor 104.

The piezoelectric sensor 104 senses a displacement signal corresponding to a displacement generated by the palpation of an artery of the person. The cardiovascular system of human body pumps blood into the arteries pulsatile during each systole and creates a displacement wave throughout the arterial tree. The displacement signal is sent as a first input to the processor 110.

The processor 110 is also configured to receive a set of parameters. The set of parameters act as a second input to the processor 110. The set of parameters include at least one of a mean radius of the artery, a radius at zero mmHg, a viscoelastic damping parameter, an elasticity of the artery and a thickness of wall of the artery. The set of parameters are derived from a set of standard references present in the prior art literature.

The derivation of the set of parameters from the standard literature makes the device 100 suitable for general application. The device 100 can be used with any person irrespective of other parameters related to the person such as age, health etc. of the person. The set of parameters are varied with respect to a variance (10% of the mean) and the mean of the set of parameters estimated from the standard literature. It should be appreciated that the set of parameters are provided using the user interface 106. In another embodiment, it the set of parameters are pre-fed in the processor 110.

According to another embodiment of the invention, the device 100 can be personalized for individualized monitoring of the person. A medical history related to the blood pressure of the person is provided to the processor 110. To be more specific, an initial systolic and diastolic blood pressure values are provided to the processor. The initial systolic and diastolic values can be measured using existing blood pressure monitoring device prior to using the device 100. The initial systolic and diastolic values can also be taken from the medical history of the person. The medical history related to the systolic and diastolic blood pressure of the person is used to calculate the set of parameters specific to the person. The mean radius of the artery ($R_{mean}$), the radius of artery at zero mmHg ($R_0$), the viscoelastic damping parameter ($\gamma$), the elasticity of the blood vessel ($H_0$) and the thickness of the wall of the artery are calculated specifically for the person. In an example, the medical history related to the blood pressure of the person is provided using the user interface 106. In another example, medical history related to the blood pressure of the person can be provided as input using any other means such as during the registration process of a person in the health care facility. In another example, the medical history related to the blood pressure of the person can be programmed using a cloud software update.

The processor 110 includes a plurality of modules for performing various functions. The plurality of modules include modules such as a signal processing module 112, a receiving module (not shown), an optimization module (not shown), etc. The signal processing module 112 may further include a pre-amplifier and a filter (not shown).

The processor 110 makes use of a predefined model for the estimation of the blood pressure of the person. The model is used for monitoring the blood pressure of the person using a "constitutive model" of the radial artery and surrounding tissues. The model is governed by the set of parameters as defined above. In another embodiment the model may also consider few other parameters in addition to the set of parameters.

According to an embodiment of the invention, the constitutive model may include a mathematical model of a voight-type viscoelastic cylinder. This model has been frequently used in the art for modelling an artery. The mathematical model of a voight-type viscoelastic cylinder is used to model the radial artery at the region of interest. The region of interest includes 1-5 cm below the dorsal side of the styloid process landmark on the surface of the wrist. The model is governed by the set of parameters. The set of parameters include the mean radius of the artery ($R_{mean}$), the radius of artery at zero mmHg ($R_0$), the viscoelastic damping parameter ($\gamma$), the elasticity of the blood vessel ($H_0$) and the thickness of the wall of the artery or cylindrical structure under consideration. Normally, the elasticity of the blood vessel varies with respect to state of the cardiac cycle of the person.

In an embodiment of the invention, few of the set of parameters are estimated from the standard literature in the art, while others are estimated using the model. In another embodiment the set of parameters are estimated for individualized monitoring of the person. The mean radius of the artery ($R_{mean}$) the radius of artery at zero mmHg ($R_0$) and the elasticity of the blood vessel are estimated from the prior art. These parameters are varied with respect to a variance (10% of the mean) and the mean of the set of parameters estimated from the standard literature. The estimation of the viscoelastic damping parameter ($\gamma$), the elasticity of the blood vessel ($H_0$) are done using the model. The model is configured to relate the pressure inside the artery to the external pressure applied. The model further configured to use a Monte-Carlo sampling methodology to infer the maximum likely value of the parameters given a ground truth systolic pressure.

According to an embodiment of the invention, the set of parameters need to be optimized before providing them as the input to the model. In an example, a genetic optimization algorithm can be used to optimize the set of parameters. It should be appreciated that the use of any other optimization technique such heuristic optimization approach is well within the scope of this invention.

In the genetic optimization algorithm, a unique cost function is minimized to optimize the set of parameters. The model uses the genetic optimization algorithm for the optimization of viscoelastic damping parameter, which governs the damping caused by the surrounding tissues on the radial artery pulse waveform. The model further uses the genetic optimization algorithm for the optimization of the mean radius ($R_{mean}$) around which radial artery is pulsating at the location 2-4.5 cm below the thumb-region 3-5 cm proximal to the flexor carpi radialis. The model further uses the genetic optimization algorithm for the optimization of the radius at zero mmHg ($R_0$) which is used for finding the parameter $A_0$ in the equation around which radial artery is pulsating at the location 2-4.5 cm below the thumb-region 3-5 cm proximal to the flexor carpi radialis. The optimized values which are calculated for the viscoelastic damping parameter, the mean radius and the radius at zero mmHg are assumed to vary in the physiological range randomly around a mean with a particular variance. The blood pressure value is then estimated with respect to a certain confidence level using the proposed mathematical model.

The model also used the genetic algorithm for L1 minimization of the multi-objective fitness function. In the model, the Gaussian distribution for each of the parameters under consideration and inferred the maximum likely pressure from the sampled waveform. As the relationship between the input and output wave was nonlinear and different parameters can be fitted to different type of Gaussians with or without skewness inference problem is not trivial.

According to an embodiment of the invention, the device 100 also considers the present condition of the person and various other scenarios. The device 100 can take into consideration of a third set of parameters while estimating the blood pressure. The third set of parameters include such as the body type or the fat deposition in and around the radial artery and surrounding tissues. In addition to this, the device can also use the current status of the person during the blood pressure measurement. For example, if the person is walking or jogging or working out, depending on the current condition, the device can be manipulated to estimate the blood pressure.

Figure 3:
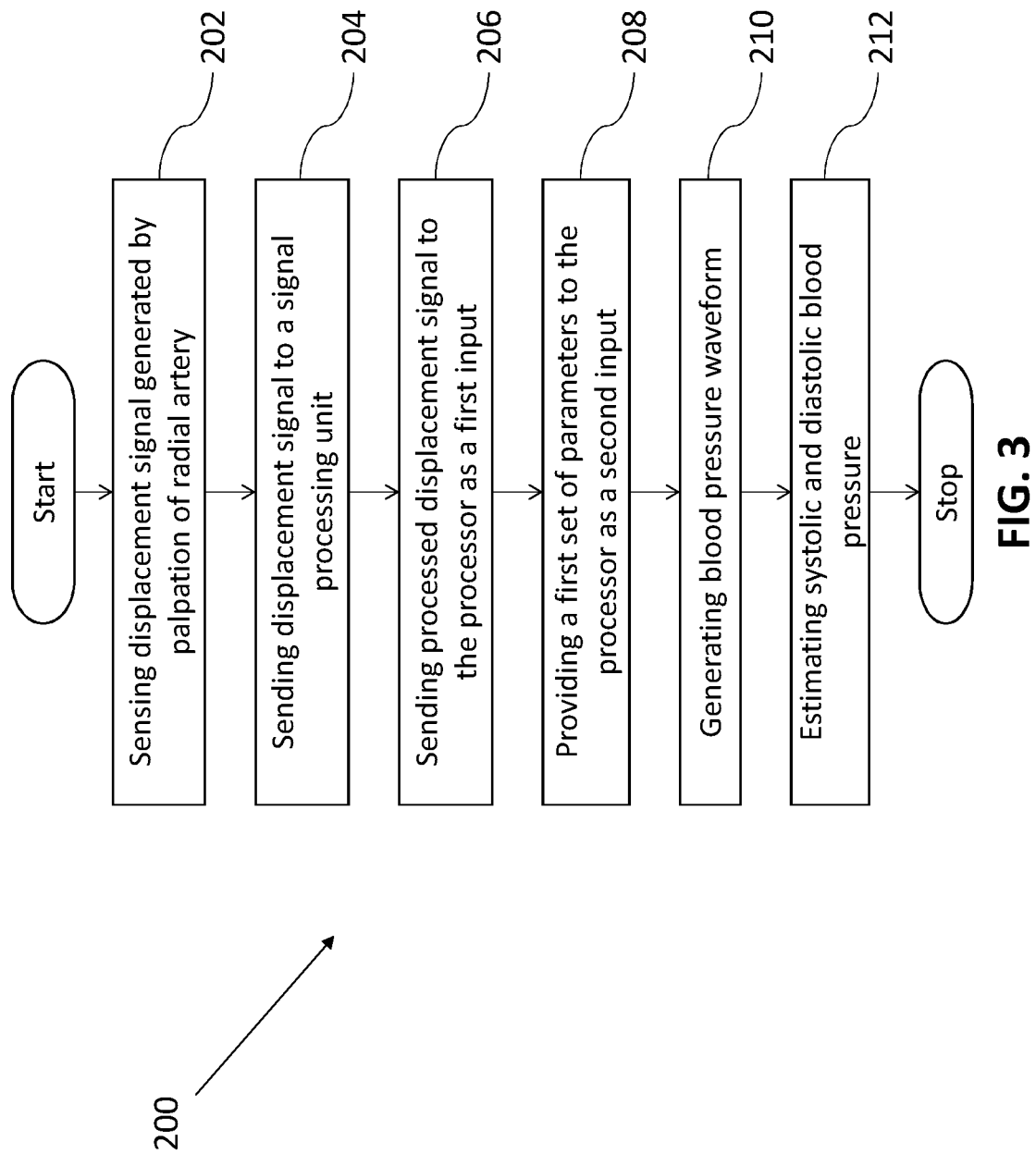
FIG. 3 shows a flow chart illustrating steps involved in blood pressure monitoring and estimation for a person in accordance with an embodiment of the invention.

According to an embodiment of the invention, the model makes use of the following formulas for the calculation of the pressure inside the artery:

$$P = P_{ext} + \frac{\beta}{A_0}(\sqrt{A} - \sqrt{A_0}) + \Gamma \frac{\partial A}{\partial t} \quad \text{Equation (1)}$$

Where $$\Gamma = (\gamma/2) * (1/\sqrt{(\pi A_0)}) \quad \text{Equation (2)}$$

$$\beta = \left(\frac{4}{3}\right)\sqrt{\pi} Eh \frac{1}{A_0} \quad \text{Equation (3)}$$

Wherein various symbols can be defined as follows:
P=Pressure inside the artery
$P_{ext}$=Pressure applied externally to the artery
A=Cross-sectional area of the artery-assuming artery is circular
$A_0$=Cross-sectional area of the artery at the zero trans-mural pressure, where the trans-mural pressure is the net pressure acting on the artery
l=Length of the arterial segment
E=Modulus of elasticity of the artery
h=Wall thickness of the artery
$\gamma$(Gamma)=Viscoelastic damping parameter or the damping coefficient According to an embodiment of the invention, a generalized method for continuously monitoring and estimating the blood pressure of the person is shown in the flowchart 200 of FIG. 3. The generalized method can be used with any person irrespective of other parameters such as age, health etc. of the person. Initially at step 202, a displacement generated by the palpation of an artery of the person. A displacement signal corresponding to the displacement is sensed by the piezoelectric sensor 104. In an embodiment, the displacement signal is sensed through the radial artery. In step 204, the displacement signal is sent to a signal processing module 112 to generate a processed displacement signal. The signal processing module 112 may also include a pre-amplifier and a filter. In step 206, the processed displacement is sent to the processor 110 as the first input.

In the next step 208, the set of parameters are provided to the processor 110 as the second input. The set of parameters include at least one of the mean radius of the artery, the radius of artery at zero mmHg, the viscoelastic damping parameter, the elasticity of the artery and the thickness of wall of the artery. The set of parameters are provided using the user interface 106. In another example, the set of parameters can also be provided using any other means. The set of parameters are derived from a set of standard references present in the prior art literature.

In the next step 210, the blood pressure waveform is generated by the processor 110 using the set of parameters and the processed displacement signal. The blood pressure waveform is displayed on the display screen 108. And finally, at step 212, the systolic blood pressure is estimated by averaging all the maximum values present in every cycle of the blood pressure waveform. Similarly, the diastolic blood pressure is estimated by averaging all the minimum values present in every cycle of the blood pressure waveform.

Figure 4:
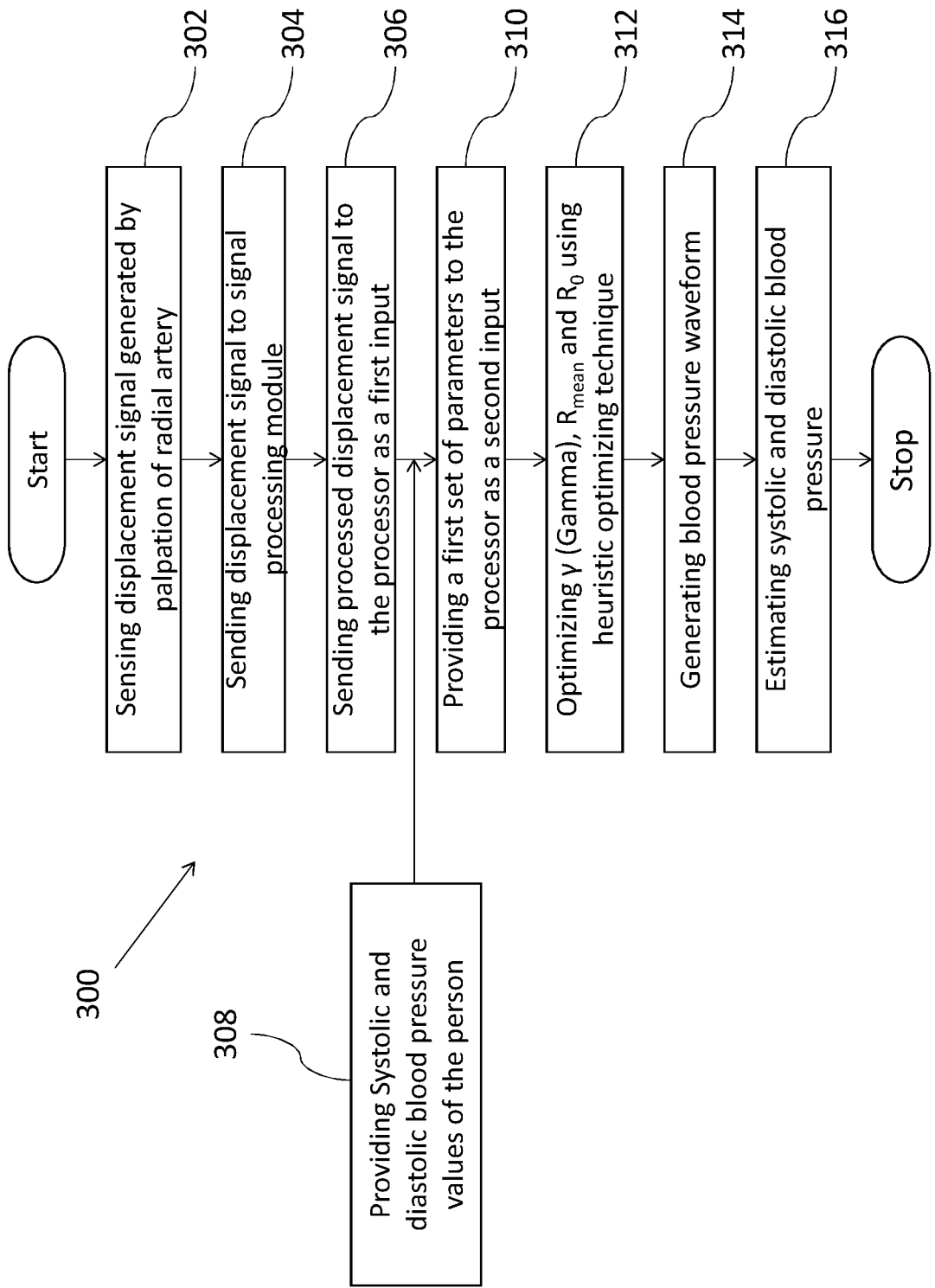
FIG. 4 shows a flow chart illustrating steps involved in blood pressure monitoring and estimation for individualized monitoring of the person in accordance with an embodiment of the invention.

According to another embodiment of the invention, a personalized method for continuously individualized monitoring and estimating the blood pressure of the person is shown in the flowchart 300 of FIG. 4. The personalized method is customized based on the medical history related to the systolic and diastolic blood pressure values of the person. Initially at step 302, a displacement generated by the palpation of an artery of the person. A displacement signal corresponding to the displacement is sensed by the piezoelectric sensor 104. In an embodiment, the displacement signal is sensed through the radial artery. In step 304, the displacement signal is sent to a signal processing module 112 to generate a processed displacement signal. The signal processing module 112 may also include a pre-amplifier and a filter. In step 306, the processed displacement is sent to the processor 110 as the first input. At step 306, the processed displacement signal is sent to the processor as the first input.

In the next step 308, the medical history related to the blood pressure of the person is provided to the processor 110. To be more specific, the systolic and diastolic blood pressure values are provided to the processor 110. The initial systolic and diastolic values can be measured using existing blood pressure monitoring device prior to using the device 100. The initial systolic and diastolic values can also be taken from the medical history of the person. In the next step 310, the set of parameters specific to the person are estimated using the medical history related to the blood pressure of the person and the processed displacement signal. The estimated set of parameters are provided to the processor 110 as the second input. The set of parameters include at least one of the mean radius of the artery, the radius of artery at zero mmHg, the viscoelastic damping parameter, the elasticity of the artery and the thickness of wall of the artery. The set of parameters are provided using the user interface 106. In another example, the set of parameters can also be provided using any other means.

In the next step 312, the viscoelastic damping parameter, the mean radius of the artery and the radius at zero mmHg are optimized by the processor 110 using a heuristic optimization technique. The viscoelastic damping parameter governs the damping caused by the surrounding tissues on the radial artery displacement signal. The radius at zero mmHg is used for finding the parameter $A_0$ in the equation (1) around which radial artery is pulsating at the location 2-4.5 cm below the thumb-region 3-5 cm proximal to the flexor carpi radialis. At the next step 314, the blood pressure waveform is generated by the processor 110. The blood pressure waveform is displayed on the display screen 108. And finally, at step 316, the systolic blood pressure is estimated by averaging all the maximum values present in every cycle of the blood pressure waveform. Similarly, the diastolic blood pressure is estimated by averaging all the minimum values present in every cycle of the blood pressure waveform.

According to an embodiment of the invention, the device is also configured to estimate a systolic blood pressure timing and a diastolic blood pressure timing. The systolic blood pressure timing is estimated by measuring a time difference between a systolic rising time and a diastolic starting time. The diastolic blood pressure timing is estimated by measuring a time difference between the diastolic starting time to a starting point of the blood pressure waveform.

According to an embodiment of the invention, the device 100 can also be used in ambulatory scenarios. In the existing blood pressure monitors, it is difficult to monitor the blood pressure when the person is moving or when the person is sleeping. The present device 100 is attached to the person for the monitoring and estimation of the blood pressure even when the person is moving or sleeping. The device 100 involves robust signal processing techniques to generate a noise free displacement signal for the estimation of the blood pressure.

According to an embodiment of the invention, the computational efficiency of the device 100 can be controlled. The computational efficiency can be controlled by using a suitable number of samples during the estimation of the blood pressure. Though by doing so, the accuracy of the estimation of the blood pressure can be reduced.

According to an embodiment of the invention, the method can also be generalized using a probabilistic technique. In this case, the device can be used with any person without customizing it every time before use.

It should be appreciated the device and method can also be used for the estimation of other parameters of the person such as heart rate, etc. It should also be appreciated that the device can also be implemented using Hrllasika based wearable nadi sensor.

In view of the foregoing, it will be appreciated that the present invention provides a method and device for the continuous estimation of the blood pressure using palpation signal captured from the artery. Still, it should be understood that the foregoing relates only to the exemplary embodiments of the present invention, and that numerous changes may be made thereto without departing from the spirit and scope of the invention as defined by the following claims.

We claim:

1. A method for non-invasively and continuously monitoring and estimating blood pressure of a person, the method comprising a processor implemented steps of:
   sensing a displacement signal generated by palpation of an artery at a region of interest of a body of the person using a piezoelectric sensor;
   generating, by the processor, a processed displacement signal by amplifying and filtering the displacement signal;
   sending the processed displacement signal as a first input to the processor; and providing a set of parameters as a second input to the processor, wherein the set of parameters include a mean radius of the artery ($R_{mean}$, a radius of the artery at zero mmHg ($R_0$), a viscoelastic damping parameter (γ), an elasticity of the artery ($H_0$), and a thickness of wall of the artery, wherein the set of parameters are estimated using the processed displacement signal and previously measured systolic and diastolic blood pressure values of the person received from a medical history of the person;

generating a blood pressure waveform as an output of the processor using a constitutive model of the artery and surrounding tissues at the region of interest of body of the person, wherein the constitutive model is a mathematical model of a Voight-type viscoelastic cylinder used to model the artery and the surrounding tissues at the region of interest, wherein the constitutive model is governed by the set of parameters comprising the viscoelastic damping parameter, the mean radius of the artery, the radius at zero mmHg, the elasticity of the artery, the thickness of the wall of the artery and the processed displacement signal, and wherein the constitutive model enables generation of the blood pressure waveform by considering fat deposition in and around the artery and surrounding tissues, wherein the constitutive model is a predefined formula used to calculate a pressure inside the artery, the predefined formula is $$P = P_{ext} + \frac{\beta}{A_0}(\sqrt{A} - \sqrt{A_0}) + \Gamma \frac{\partial A}{\partial t}, \text{ wherein}$$

$$\Gamma = (\gamma/2) * (1/\sqrt{(\pi A_0)}) \text{ and } \beta = \left(\frac{4}{3}\right)\sqrt{\pi} \, Eh \frac{1}{A_0},$$

wherein
P=Pressure inside the artery
$P_{ext}$=Pressure acting externally to the artery
A=Cross-sectional area of the artery by taking artery is circular
$A_0$=Cross-sectional area of the artery at the zero trans-mural pressure, where the trans-mural pressure is the net pressure acting on the artery
l=Length of the arterial segment
E=Modulus of elasticity of the artery
h=Wall thickness of the artery
γ(Gamma)=Viscoelastic damping parameter or the damping coefficient, wherein the viscoelastic damping parameter, the mean radius of the artery and the radius of artery at zero mmHg are optimized by using a heuristic optimization technique, and wherein the radius of the artery at zero mmHg is used for finding the parameter '$A_0$' in the formula around which the artery is pulsating at the region of interest, wherein the said blood pressure waveform is generated by the constitutive model by relating the pressure inside the artery to an external pressure acting on the artery, wherein the viscoelastic damping parameter governs damping caused by the surrounding tissues on the displacement signal; and
estimating, by the processor, a systolic blood pressure and a diastolic blood pressure using maximum and minimum values respectively of the blood pressure waveform.

2. The method of claim 1 further includes estimating a systolic blood pressure time by measuring a time difference between a systolic rise time to a diastolic start time using the said blood pressure waveform.

3. The method of claim 1 further includes estimating a diastolic blood pressure time by measuring a time difference between a diastolic start time to a start of the said blood pressure waveform.

4. The method of claim 1 further includes displaying the blood pressure waveform on a display screen.

5. The method of claim 1, wherein the processor further measures heart rate of the person.

6. The method of claim 1 further includes the step of controlling the efficiency of the blood pressure measurement using a predefined number of samples of the blood pressure waveform.

7. A non-transitory computer-readable medium having embodied thereon a computer program executed by a processor for performing a method for non-invasively and continuously monitoring and estimating blood pressure of a person, the method comprising:
sensing a displacement signal generated by palpation of an artery at a region of interest of a body of the person using a piezoelectric sensor;
generating, by the processor, a processed displacement signal by amplifying and filtering the displacement signal;
sending the processed displacement signal as a first input to the processor; and
providing a set of parameters as a second input to the processor, wherein the set of parameters include a mean radius of the artery ($R_{mean}$), a radius of the artery at zero mmHg ($R_0$), a viscoelastic damping parameter (γ), an elasticity of the artery ($H_0$) and a thickness of wall of the artery, wherein the set of parameters are estimated using the displacement signal and previously measured systolic and diastolic blood pressure values of the person received from a medical history of the person;
generating a blood pressure waveform as an output of the processor using a constitutive model of the artery and surrounding tissues at the region of interest of body of the person, wherein the constitutive model is a mathematical model of a Voight-type viscoelastic cylinder used to model the artery and the surrounding tissues at the region of interest, wherein the constitutive model is governed by the set of parameters comprising the viscoelastic damping parameter, the mean radius of the artery, the radius of the artery at zero mmHg, the elasticity of the artery, the thickness of the wall of the artery and the processed displacement signal, and, wherein the constitutive model is a predefined formula used to calculate a pressure inside the artery, the predefined formula $$P = P_{ext} + \frac{\beta}{A_0}(\sqrt{A} - \sqrt{A_0}) + \Gamma \frac{\partial A}{\partial t}, \text{ wherein}$$

$$\Gamma = (\gamma/2) * (1/\sqrt{(\pi A_0)}) \text{ and } \beta = \left(\frac{4}{3}\right)\sqrt{\pi} \, Eh \frac{1}{A_0},$$

is
wherein
P=Pressure inside the artery
$P_{ext}$=Pressure acting externally to the artery
A=Cross-sectional area of the artery by taking artery is circular
$A_0$=Cross-sectional area of the artery at the zero trans-mural pressure, where the trans-mural pressure is the net pressure acting on the artery
l=Length of the arterial segment
E=Modulus of elasticity of the artery
h=Wall thickness of the artery
γ(Gamma)=Viscoelastic damping parameter or the damping coefficient, wherein the viscoelastic damping parameter, the mean radius of the artery and the radius of artery at zero mmHg are optimized by using a heuristic optimization technique, and wherein the radius of the artery at zero mmHg is used for finding the parameter '$A_0$' in the formula around which the artery is pulsating at the region of interest, and wherein the constitutive model enables generation of the blood pressure waveform by considering fat deposition in and around the artery and surrounding tissues, wherein the said blood pressure waveform is generated by the constitutive model by relating the pressure inside the artery to an external pressure acting on the artery, wherein the viscoelastic damping parameter governs damping caused by the surrounding tissues on the displacement signal; and estimating a systolic blood pressure and a diastolic blood pressure using maximum and minimum values respectively of the blood pressure waveform.

\* \* \* \* \*